United States Patent
Drai

(10) Patent No.: US 12,186,325 B2
(45) Date of Patent: Jan. 7, 2025

(54) TREATMENT AND PREVENTION OF PREMATURE EJACULATION (PE)

(71) Applicant: SEROJAC PME Handels GmbH, Vienna (AT)

(72) Inventor: Daniel Drai, Givataim (IL)

(73) Assignee: SEROJAC PME HANDELS GMBH, Vienna (AT)

( * ) Notice: Subject to any disclaimer, the term of this patent is extended or adjusted under 35 U.S.C. 154(b) by 732 days.

(21) Appl. No.: 17/290,038

(22) PCT Filed: Oct. 30, 2019

(86) PCT No.: PCT/EP2019/079584
§ 371 (c)(1),
(2) Date: Apr. 29, 2021

(87) PCT Pub. No.: WO2020/089261
PCT Pub. Date: May 7, 2020

(65) Prior Publication Data
US 2021/0401852 A1   Dec. 30, 2021

(30) Foreign Application Priority Data

Oct. 30, 2018 (EP) .................................... 18203410

(51) Int. Cl.
*A61K 31/55* (2006.01)
*A61K 31/475* (2006.01)
*A61P 15/00* (2006.01)

(52) U.S. Cl.
CPC ............ *A61K 31/55* (2013.01); *A61K 31/475* (2013.01); *A61P 15/00* (2018.01)

(58) Field of Classification Search
CPC .. A61K 31/55; A61K 31/475; A61K 2300/00; A61P 15/00
See application file for complete search history.

(56) References Cited

U.S. PATENT DOCUMENTS

| | | | | |
|---|---|---|---|---|
| 5,922,341 A | * | 7/1999 | Smith .................... | A61K 45/06 424/433 |
| 6,495,154 B1 | | 12/2002 | Tam et al. | |
| 2002/0161016 A1 | * | 10/2002 | Tam ...................... | A61K 31/135 514/278 |
| 2007/0043030 A1 | | 2/2007 | Morton et al. | |

FOREIGN PATENT DOCUMENTS

| | | | | |
|---|---|---|---|---|
| CN | 1241435 A | * | 1/2000 | |
| CN | 103948742 | * | 4/2017 | |
| WO | WO 02/40027 A1 | | 5/2002 | |
| WO | WO 02/41883 A2 | | 5/2002 | |
| WO | WO 2005/025550 A1 | | 3/2005 | |
| WO | WO-2013002578 | * | 1/2013 | ............ A61K 31/55 |

OTHER PUBLICATIONS

Brito, https://www.medicalnewstoday.com/articles/327388#is-there-a-permanent-cure) (Year: 2022).*
Jeon et al. (WO 2013002578, see English translation) (Year: 2013).*
CN103948742—English translation (Year: 2017).*
CN 1241435A—English translation (Year: 2000).*
Extended European Search Report issued May 7, 2019 in European Patent Application No. 18203410.8, 8 pages.
International Search Report issued Feb. 13, 2020 in PCT/EP2019/079584 filed Oct. 30, 2019, 4 pages.
J. T. Hsieh, et al., "An in vivo evaluation of the therapeutic potential of sympatholytic agents on premature ejaculation," BJU International, vol. 84, XP055583056, 1999, pp. 503-506.
Marcel D. Waldinger, "Drug treatment options for premature ejaculation," Expert Opinion on Pharmacotherapy, vol. 19, No. 10, XP055583079, 2018, 10 pages.
Catherine H. Mercer, et al., "Sexual function problems and help seeking behaviour in Britain: national probability sample survey," BMJ, vol. 327, Aug. 23, 2003, pp. 426-427.
Francesco Montorsi, "Prevalence of Premature Ejaculation: A Global and Regional Perspective," J. Sex. Med., Supplement 2, 2005, pp. 96-102.
Chris G. McMahon, "Dapoxetine: a new option in the medical management of premature ejaculation," Therapeutic Advances in Urology, vol. 4, No. 5, 2012, pp. 233-251.
Kate D. Linton, et al., "Recent advances in the treatment of premature ejaculation," Drug Design, Development and Therapy, vol. 4, 2010, pp. 1-6.
Sae Chul Kim, et al., "Efficacy and safety of fluoxetine, sertraline and clomipramine in patients with premature ejaculation: a double-blind, placebo controlled study," The Journal of Urology, vol. 159, Issue 2, Feb. 1998, 3 pages (submitting Abstract only).
Marcel D. Waldinger, et al., "On-Demand Treatment of Premature Ejaculation with Clomipramine and Paroxetine: A Randomized, Double-Blind Fixed-Dose Study with Stopwatch Assessment," European Urology, vol. 46, 2004, pp. 510-516.
Price J, et al. "Treatment of clomipramine-induced anorgasmia with yohimbine: a case report," J. Clin. Psychiatry, vol. 51, No. 1, Jan. 1990, 1 page (submitting Abstract only).
Yves Lecrubier, et al., "Favourable effects of yohimbine on clomipramine-induced orthostatic hypotension: a double-blind study," Br. J. Clin. Pharmacol., vol. 12, 1981, pp. 90-93.
L. Lacomblez, et al., "Effect of yohimbine on blood pressure in patients with depression and orthostatic hypotension induced by clomipramine," Clin. Pharmacol. Ther., vol. 45, No. 3, Mar. 1989, pp. 241-251.

(Continued)

*Primary Examiner* — Umamaheswari Ramachandran
(74) *Attorney, Agent, or Firm* — Merchant & Gould P.C.; Daniel Pereira

(57) ABSTRACT

A pharmaceutical composition may include clomipramine or a pharmaceutically acceptable salt form thereof and yohimbine or a pharmaceutically acceptable salt form thereof and may be used in the treatment and prevention of premature ejaculation. The composition may contain, for example, 5 to 150 mg clomipramine, and/or, for example, 5 to 150 mg yohimbine.

14 Claims, No Drawings

(56) References Cited

OTHER PUBLICATIONS

Sheshadri Shekar, et al., "Effect of yohimbine on clomipramine-induced sexual dysfunction in male rats," Asian Journal of Pharmaceutical and Clinical Research, vol. 10, Issue 2, 2017, pp. 92-96.
Hollander E., et al., "Yohimbine treatment of sexual side effects induced by serotonin reuptake blockers," J. Clin. Psychiatry, vol. 53, No. 6, Jun. 1992, 1 page (submitting Abstract only).
Marc G. Sturgill, et al., "Yohimbine Elimination in Normal Volunteers Is Characterized by Both One- and Two-Compartment Behavior," Journal of Cardiovascular Pharmacology, vol. 29, No. 6, Jun. 1997, 11 pages (Jan. 3, 2024).
A. Morales, "Yohimbine in Erectile Dysfunction: the Facts", International Joural of Impotence Research, (2000) 12, Suppl 1, pp. S70-S74.
Lawrence C. Jenkins, M.D., MBA, et al., "Delayed Orgasm and Anorgasmia", Fertility and Sterility® vol. 104, No. 5, Nov. 2015, pp. 1082-1088.
Christopher H. Linden, MD, et al., "Yohimbine: A New Street Drug", Annals of Emergency Medicine, (14), Oct. 10, 1985, pp. 1002/115-1004/117.
Elizabeth Jing, et al., "Sexual dysfunction in selective serotonin reuptake inhibitors (SSRIs) and potential solutions: A narrative literature review," Ment Health Clin [Internet]. 2016;6(4):191-6. DOI: 10.9740/mhc.2016.07. pp. 191-196.
Ibrahim A. Abdel-Hamid, et al., "The Drug Treatment of Delayed Ejaculation", Transl Androl Urol 2016;5(4):576-591.
Request for International Preliminary Examination dated Aug. 28, 2020, in International Patent Application No. PCT/EP2019/079584.
Office Action issued Mar. 21, 2024, in corresponding Chinese Patent Application No. 201980071506.2 with English language translation. (Cite No. 3 reference is cited herein).
Decision of Refusal dated Mar. 15, 2024, in Japanese Patent Application No. 2021-524403 (with partial English translation).
Haibo Shi, et al., "Common Knowledge: Latest Clinical Drug Manual", Liaoning Science and Technology Press, p. 421 (2016).
Combined Chinese Office Action and Search Report issued Aug. 2, 2023 in Chinese Patent Application No. 201980071506.2 (with English Translation), 13 pages.
Hollander et al., "Yohimbine treatment of sexual side effects induced by serotonin reuptake blockers", J Clin Psychiatry, vol. 54, No. 3, Mar. 1993, 1 page.

\* cited by examiner

TREATMENT AND PREVENTION OF PREMATURE EJACULATION (PE)

The present invention relates to treatment and prevention of premature ejaculation (PE).

PE, early or rapid ejaculation is the most common sexual disorder, affecting men with a prevalence around 10% lasting 1 month in the previous year and a lifetime prevalence of approximately 30% (Mercer et al., BMJ 327 (2003), 426-427; Montorsi, J Sex Med 2 (2005), Suppl 2, 96-102). Neither drug has been approved in the EC or by FDA in the indication PE as single agent nor has been approved for any indication worldwide in combination. Except for Dapoxetine (Priligy®; McMahon, Ther Adv Urol 4 (2012), 233-251), there are no pharmaceutical agents approved in the EC or by FDA for PE, thus most currently available used for this condition are off label. In addition, Dapoxetine has been controversially discussed both regarding efficacy and safety underlining a high unmet medical need for an approved pharmacological alternative (Linton et al., Drug Des Devel Ther 4(2010), 1-6).

WO 03/000343 A2 suggests to use phosphodiesterase inhibitors, such as tadalafil, vardenafil and sildenafil, for treating premature ejaculation, Some psychoactive drugs, particularly tricyclic antidepressants, such as clomipramine, and selective serotonin reuptake inhibitors (SSRIs), such as fluoxetine, paroxetine and sertraline, can delay ejaculation as a side effect. Almost all members of the SSRI family have been shown to be able to delay ejaculation, though to various extents. Clomipramine is a chlorinated analogue of imipramine with both antidepressant and antiobsessional properties, which penetrates the blood-brain barrier readily, reaching concentrations in the brain that are ten times greater than plasma concentrations after a single parenteral dose. Clomipramine inhibits norepinephrine and serotonin uptake into central nerve terminals, possibly by blocking the membrane-pump of neurons, thereby increasing the concentration of transmitter monoamines at receptor sites. Clomipramine also possesses anticholinergic properties, weak antihistamine and antiserotonin properties, potentiates the effect of norepinephrine and other drugs acting on the central nervous system, has a quinidine-like effect on the heart and may impair cardiac conduction. Clomipramine has been shown to block ejaculation without suppressing orgasm. Clomipramine has an effect on the excretory phase of ejaculation, by inhibiting contraction of the longitudinal fibers of the deferent ducts responsible for the sperm progression, without affecting the contractile activity of their circular fibers which act as a clamp, blocking the passage of the semen. A significant increase in time to ejaculation has been demonstrated in men who took 25 milligrams of clomipramine 12 to 24 hours before anticipated sexual activity. The latency to ejaculation ranged from about 1.5 to 2 minutes up to about 8 minutes, which was considered to be in the range in which sexual satisfaction was reported. Another study reported that 50 mg of clomipramine can extend time to climax in premature ejaculators to more than 8 minutes. In most available studies on PE, clomipramine was used as on demand treatment. With chronic use adverse events of clomipramine and other antidepressants increases (Kim et al., J Urol 159 (1998), 425-427). WO 2007/000764 A2 discloses a pharmaceutical composition comprising a pharmaceutically effective amount of an erection-enhancing agent, such as tadalafil, vardenafil and sildenafil, and a pharmaceutically effective amount of an ejaculation-delaying agent, such as clomipramine, wherein an efficacy window of the erection-enhancing agent and the efficacy window of said ejaculation-delaying agent should substantially overlap; however, also this approach did not result in clinical success or market authorization.

Therefore, there is still an urgent and unmet need to provide proper medication for the treatment and prevention of PE. Moreover, it is a specific object of the present invention to provide an improved PE treatment comprising clomipramine but with lower or without the risk of the adverse reactions usually connected with clomipramine administration or with increased efficacy or with more convenient mode of administration.

Therefore, the present invention provides a pharmaceutical composition comprising clomipramine (3-(3-chloro-10, 11-dihydro-5H-dibenzo[b,f]azepin-5-yl)-N,N-dimethylpropan-1-amine) or a pharmaceutically acceptable salt form thereof and yohimbine (17α-hydroxy-yohimban-16α-carboxylic acid methyl ester) or a pharmaceutically acceptable salt form thereof for use in the treatment and prevention of premature ejaculation (PE).

The present invention therefore provides a new and improved combination treatment regimen using clomipramine but with significantly decreased risk of adverse reactions (side effects; see Kim et al., 1998) and/or (depending mainly on the amounts of clomipramine administered or compared to clomipramine alone or combined with other erection-enhancing agent, such as tadalafil, vardenafil and sildenafil) with increased efficacy.

Clomipramine is a tricyclic antidepressant that inhibits the reuptake of noradrenaline and serotonin. It is commonly used in the treatment of obsessive-compulsive disorders. To treat psychiatric disorders, clomipramine is given as 10-25 mg/day initially, and increasing gradually to 25 to 150 mg/day and more, if required, divided into several doses throughout the day or as a single dose at bedtime (Anafranil®). Many patients are adequately maintained on doses between 50-100 mg/day.

When used to treat psychiatric disorders it was shown that 96% of males and females on clomipramine suffered from delayed orgasm representing the highest rate of antidepressant-induced sexual dysfunction with any medication and it was consistent with clomipramine's potent serotonergic activity. Compared to other tricyclic antidepressants, it has a greater effect on dopamine blockade and serotonin reuptake inhibition. These implicate for prolactin release and orgasmic dysfunction mediated through 5-HT2 receptors. Moreover, peripheral antimuscarinic and a adrenergic blockade have been implicated as cause of clomipramine-induced sexual dysfunction. Regarding treatment of PE, studies with clomipramine monotherapy as continuous dosing as well as on-demand dosing have shown increases in the intravaginal ejaculation latency time (IELT). In particular, on-demand treatment with 25 mg clomipramine led to a 4.05 (95% CI:3.26-5.02) fold-increase of the IELT (Waldinger et al., Eur Urol 46 (2004), 510-515). In South Korea clomipramine is given as on demand treatment for PE using 15 mg (Condencia®). However, the pharmacokinetic of clomipramine shows a high variability between patients, e.g. 75 mg clomipramine daily produces steady state concentrations of clomipramine ranging from about 20 to 175 ng/ml. Following single oral doses of 50 mg and 100 mg in healthy volunteers peak plasma concentrations of clomipramine of 28.8±11.2 ng/ml (range 16.5 to 53 ng/ml at 3 to 5 hours post-dose) and 70-140 ng/ml (at 1 to 2.5 hours post-dose), respectively have been reported. Peak plasma concentrations of desmethylclomipramine (an active metabolite) of 5.0±1.4 ng/ml (range 2.9 to 7.8 ng/ml) have been reported to occur between 5 to 12 hours after a single oral dose of 50 mg. Oral clomipramine is eliminated from the blood with a mean half-life of 21 hours (range 12-36 h), and desmethylclomipramine with a half-life of 36 hours (up to 9 hours). Accordingly, steady state concentra-tions are not achieved before several days to weeks. It is therefore preferred for the present invention to administer clomipramine by continuous dosing to treat PE.

As described above, many patients are adequately maintained on doses between 50-100 mg clomipramine/day. However, according to the present invention it is preferred to use lower dosage and to keep the dose for treating PE below 50 mg per day in order to remain below the dose that is therapeutically used in psychiatric disorders.

Accordingly, the pharmaceutical composition according to the present invention may generally contain the amounts and dosages known for clomipramine to be administered, for example from 5 to 150 mg clomipramine (clomipramine amounts are meant to be defined as mg of the clomipramine base). Preferably, however, lower dosages of clomipramine are used as in such typical clomipramine regimen, for example only half or a third of usual clomipramine amounts. Accordingly, a preferred composition according to the present invention contains 10 to 50 mg clomipramine, especially 20 to 40 mg.

Clomipramine is used commercially almost exclusively as the hydrochloride salt; however, other salt forms as well as the free base may also be used according to the present invention.

Yohimbine is reported to improve sexual activity by involving noradrenaline and dopamine of central origin and to improve sexual behavioural parameters. Additionally, direct vasodilatation in the penis seems to play a role. Animal studies confirm that yohimbine improves erectile dysfunction in aged male rats. A limited number of single-dose pharmacokinetic studies of yohimbine administered by the oral or intravenous routes indicate one- or two-compartmental elimination, with an elimination half-life <1 h, although an active metabolite (11-hydroxy-yohimbine) exhibits a much longer elimination half-life of 6 h. In addition, oral administration is associated with highly variable bioavailability (between 7 and 87%), which appears to be the result of extensive hepatic first-pass metabolism. Hsieh et al. (BJU international 84.4 (1999): 503-506) report that sympatholytic agents including yohimbine can suppress seminal vesicle contractile response to electrical nerve stimulation.

Also for yohimbine, the established dosages may be applied; however, also here, lower doses are preferred (optionally titrated for the individual patient). Accordingly, the pharmaceutical composition according to the present invention preferably contains 5 to 150 mg yohimbine (yohimbine amounts are meant to be defined as mg of the yohimbine methyl ester). According to preferred embodiments of the present invention, the composition contains 10 to 50 mg yohimbine, especially 20 to 40 mg.

Also yohimbine is used commercially almost exclusively as the hydrochloride salt; however, other salt forms as well as the free ester may also be used according to the present invention.

Clomipramine and yohimbine were used in the prior art as combination treatments, however, those reports were pointing into a completely different direction so that the effective use of this combination for the treatment and prevention (or amelioration and alleviation) of PE was surprising.

For example, Price et al. (J Clin Psychiatry 51 (1990), 32-33) reported a successful treatment of clomipramine-induced anorgasmia with yohimbine in a patient with obsessive compulsive disorder and major depression. Lecrubier et al. (J Clin Pharmacol 12 (1981), 90-93) showed that yohimbine had favourable effects on orthostatic hypotension induced by clomipramine (confirmed by Lacomblez et al., Clin Pharmacol Ther 45 (1989), 241-51). Shekar et al. (Asian J Pharm Clin Res 10 (2017), 92-96) showed that yohimbine failed to antagonize the clomipramine-induced sexual dysfunction in male rats. Hollander et al. (J Clin Psychiatry 53 (1992), 207-209) reported that five of six patients who suffered sexual side effects (sexual disfunction) in the course of clomipramine treatment experienced improved sequal functioning after yohimbine treatment. Of course, no one of these reports referred to the treatment of PE nor suggested to use or indicated to use clomipramine and yohimbine for the treatment of PE, of course not for patients who have not (yet) been treated with clomipramine.

WO 2005/025550 A1 relates to pharmaceutical compositions comprising an antidepressant, which can be clomipramine, for treating PE by pulmonary inhalation. WO 02/41883 A2 also discloses a method for treatment of PE by administration of an antidepressant drug which can be a tricyclic antidepressant such as clomipramine. Both documents mention yohimbine in laundry lists of hundreds of additional active agents that can be included in the pharmaceutical composition or co-administered with the antidepressant. However these documents do not provide any rational for any combination or disclose any effect of including one of the hundreds of listed compounds. Moreover, they do not provide an enabling disclosure for preparing or administering any such a combination.

In the course of the present invention it was surprisingly found that combining yohimbine with clomipramine improves the efficacy of clomipramine (increases IELT) and at the same time reduces side effects associated with clomipramine treatment such as dizziness, dyspepsia and constipation (see Case Reports herein below). Both the increased efficacy and the reduced adverse side effects were completely unexpected based on the prior art.

The pharmaceutical composition according to the present invention contains clomipramine and yohimbine in a molecular ratio of clomipramine to yohimbine is from 0.2 to 5, preferably from 0.5 to 2, especially from 0.8 to 1.5.

Administration of the composition according to the present invention is possible by all administration routes authorised for clomipramine and/or yohimbine. Oral administration is preferred. Although a once a day administration is the most convenient way of administering the pharmaceutical composition according to the present invention, the composition may also be administered more than once a day, for example twice or three times per day to a patient suffering from PE or being at risk of suffering from PE. In general, administration frequency and dosages are usually driven by the need to keep a certain plasma level of clomipramine and/or yohimbine, for example a peak plasma level of clomipramine at 20 ng/ml or higher.

For yohimbine, a preferred plasma level to be provided within the course of the present invention is a peak plasma level of yohimbine at 50 ng/ml or higher (Sturgill et al., J Cardiovasc Pharmacol, 1997. 29(6): p. 697-703).

In principle, the PE treatment of the present invention may be applied to any PE patient in need of treatment or prevention of PE (e.g. also for patients which have a risk for developing PE). The "treatment" according to the present invention also includes a significant alleviation or amelioration of PE.

Particularly preferred are patients having the following features, the following PE medical history, or the following risk factors for developing PE: Primary PE and secondary or acquired PE. The latter is a small group, i.e. less than 10% of the patients who complain about PE.

The present invention is specifically suitable to treat patients who have not been treated with clomipramine in the past or who have not been treated with clomipramine in the recent past, e.g. in the last year or the last 6 months. The combination of clomipramine with yohimbine can help them to treat the secondary sexual effects of psychiatric treatment with clomipramine only such as anorgasmia.

The pharmaceutical composition according to the present invention usually comprises a pharmaceutically acceptable carrier. Oral dosage forms suitable for the present invention include tablets, capsules, caplets, solutions, suspensions and/or syrups, and may also comprise a plurality of granules, beads, powders or pellets that may or may not be encapsulated or sublingual formulations. Such dosage forms are prepared using conventional methods known to those in the field of pharmaceutical formulation and described in the pertinent text books. Tablets and capsules represent the most convenient oral dosage forms, in which case solid pharmaceutical carriers are employed. Tablets may be manufactured using standard tablet processing procedures and equipment. One method for forming tablets is by direct compression of a powdered, crystalline or granular composition containing the active agent (s), alone or in combination with one or more carriers, additives, or the like. As an alternative to direct compression, tablets can be prepared using wet-granulation or dry-granulation processes. Tablets may also be molded rather than compressed, starting with a moist or otherwise tractable material; however, compression and granulation techniques are preferred. In addition to the active agent (s), tablets prepared for oral administration for the present invention may contain other materials such as binders, diluents, lubricants, disintegrants, fillers, stabilizers, surfactants, coloring agents, and the like. Binders are used to impart cohesive qualities to a tablet, and thus ensure that the tablet remains intact after compression. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, ethyl cellulose, hydroxyethyl cellulose, and the like), and Veegum. Diluents are typically necessary to increase bulk so that a practical size tablet is ultimately provided. Suitable diluents include dicalcium phosphate, calcium sulfate, lactose, cellulose, kaolin, mannitol, sodium chloride, dry starch and powdered sugar. Lubricants are used to facilitate tablet manufacture; examples of suitable lubricants include, for example, magnesium stearate, calcium stearate, and stearic acid. Stearates, if present, preferably represent at no more than approximately 2 wt. % of the drug-containing core. Disintegrants are used to facilitate disintegration of the tablet, and are generally starches, clays, celluloses, algins, gums or cross-linked polymers. Fillers include, for example, materials such as silicon dioxide, titanium dioxide, alumina, talc, kaolin, powdered cellulose and microcrystalline cellulose, as well as soluble materials such as mannitol, urea, sucrose, lactose, dextrose, sodium chloride and sorbitol. Stabilizers are used to inhibit or retard drug decomposition reactions that include, by way of example, oxidative reactions. Surfactants may be anionic, cationic, amphoteric or nonionic surface active agents. The dosage form may also be a capsule, in which case the active agent-containing composition may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. If the active agent-containing composition is present within the capsule in liquid form, a liquid carrier is necessary to dissolve the active agent (s). The carrier must be compatible with the capsule material and all components of the pharmaceutical composition, and must be suitable for ingestion. Solid dosage forms, whether tablets, capsules, caplets, or particulates, may, if desired, be coated so as to provide for delayed release. Dosage forms with delayed release coatings may be manufactured using standard coating procedures and equipment. Such procedures are known to those skilled in the art and described in the pertinent text books. Generally, after preparation of the solid dosage form, a delayed release coating composition is applied using a coating pan, an airless spray technique, fluidized bed coating equipment, or the like. Delayed release coating compositions comprise a polymeric material, e.g., cellulose butyrate phthalate, cellulose hydrogen phthalate, cellulose proprionate phthalate, polyvinyl acetate phthalate, cellulose acetate phthalate, cellulose acetate trimellitate, hydroxypropyl methylcellulose phthalate, hydroxypropyl methylcellulose acetate, dioxypropyl methylcellulose succinate, carboxymethyl ethylcellulose, hydroxypropyl methylcellulose acetate succinate, polymers and copolymers formed from acrylic acid, methacrylic acid, and/or esters thereof. Sustained release dosage forms provide for drug release over an extended time period, and may or may not be delayed release. Generally, as will be appreciated by those of ordinary skill in the art, sustained release dosage forms are formulated by dispersing a drug within a matrix of a gradually bioerodible (hydrolyzable) material such as an insoluble plastic, a hydrophilic polymer, or a fatty compound, or by coating a solid, drugcontaining dosage form with such a material. Insoluble plastic matrices may be comprised of, for example, polyvinyl chloride or polyethylene. Hydrophilic polymers useful for providing a sustained release coating or matrix cellulosic polymers include, without limitation: cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylcellulose phthalate, cellulose hexahydrophthalate, cellulose acetate hexahydrophthalate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate, with a terpolymer of ethyl acrylate, methyl methacrylate and trimethylammonioethyl methacrylate chloride (sold under the tradename Eudragit RS) preferred; vinyl polymers and copolymers such as polyvinyl pyrrolidone, polyvinyl acetate, polyvinylacetate phthalate, vinylacetate crotonic acid copolymer, and ethylenevinyl acetate copolymers; zein; and shellac, ammoniated shellac, shellacacetyl alcohol, and shellac n-butyl stearate. Fatty compounds for use as a sustained release matrix material include, but are not limited to, waxes generally (e.g., carnauba wax) and glyceryl tristearate.

According to a preferred embodiment, the pharmaceutical composition according to the present invention is a tablet formulation.

The present invention may be provided as a single combination medicament comprising clomipramine and yohimbine or as a medicament kit comprising a pharmaceutical composition of clomipramine and a pharmaceutical composition of yohimbine for use in the treatment or prevention of PE. Administration of the kit is then performed as co-administration. Co-administration includes administering clomipramine and yohimbine separately but as part of the same therapeutic treatment program or regimen. The components need not necessarily be administered at essentially the same time, although they can if so desired. Thus, such co-administration includes, for example, administering clomipramine and yohimbine as separate dosages or dosage forms, but at the same time.

According to another aspect, the present invention provides a method for treatment or prevention of PE wherein an effective amount of clomipramine or a pharmaceutically acceptable salt form thereof and yohimbine or a pharmaceutically acceptable salt form thereof are administered to a patient suffering from PE or being at risk of suffering from PE.

The present invention also relates to the use of clomipramine or a pharmaceutically acceptable salt form thereof and yohimbine (17α-hydroxy-yohimban-16α-carboxylic acid methyl ester) or a pharmaceutically acceptable salt form thereof for the manufacture of a medicament or a kit of medicaments for use in the treatment and prevention of PE.

The present invention will be further illustrated by the following examples, yet without being restricted thereto.

EXAMPLES

In personal clinical experience, clomipramine is dosed between 15 and 30 mg once a day, combined with yohimbine 2 mg, 6 tablets a day (total daily dose 12 mg) with good subjective success both from an efficacy and tolerability perspective.

Case Reports

Case Report 1

A 32 year old patient with a history of primary PE (who was treated unsuccessfully with paroxetine from 20 to 40 mg daily for 6 months received clomipramine doses of 30 mg once a day for weeks combined with yohimbine 2 mg, 6 tablets a day (total daily dose 12 mg). The treatment was well tolerated and the patient reported an improvement in time IELT from half a minute of penetration before ejaculation to nine minutes without the need to practice suspension exercises.

Case Report 2

A 48 year old patient with a history of primary PE (who was treated unsuccessfully with sertraline 50-100 mg for 16 weeks received clomipramine doses of 30 mg once a day for 4 weeks combined with yohimbine 2 mg, 6 tablets a day (total daily dose 12 mg). The treatment was well tolerated and the patient reported an increasing of the IELT from 1 min to 12 minutes.

Case Report 3

A 20 year old patient with a history of primary PE (who was not treated before received clomipramine doses of 15 mg once a day for 4 days combined with yohimbine 2 mg, 3 tablets a day (total daily dose 6 mg). The treatment was well tolerated and the patient reported improvement of IELT from 2 minutes to 7 minutes.

Case Report 4

A 66 year old patient with a history of primary PE (who was treated unsuccessfully with citalopram for 4 months received clomipramine doses of 30 mg once a day for 2 weeks, and after 2 weeks the dose to 30 mg twice a day for 4 weeks combined with yohimbine 2 mg, 6 tablets a day (total daily dose 12 mg). The treatment was well tolerated and the patient reported improvement in IELT from 1 minute to 6 minutes.

Case Report 5

A 42 year old patient complained about primary PE. He had been treated with a dose of 30 mg clomipramine 6 hours before sexual intercourse, which improved IELT from 1 minute to 6 minutes. However, the patient reported dizziness, dyspepsia and constipation. The treatment was then changed to a combination of 30 mg clomipramine with 6 mg yohimbine. IELT further increased to 8 minutes and no more side effects were reported.

Case Report 6

A 53 year old patient complained about erectile dysfunction and PE. At the beginning of his treatment he received 12 mg of yohimbine daily taken in two doses, morning and evening. He described improved erections but also diarrhoea from the second day of the treatment and felt no amelioration of the time of intercourse. Treatment was then changed to a combination of 30 mg clomipramine and 6 mg yohimbine. The patient reported an improvement of IELT from 2 to 7 minutes as well as a good erection, without any more complaints about diarrhoea and dyspepsia.

Case Report 7

A 27 year old patient complained about primary PE and about psychogenic erectile dysfunction. He had taken 30 mg of clomipramine 6 hours and 100 mg of sildenafil one hour before sexual intercourse but felt bad, with low blood pressure, headaches, dizziness, and was not able to achieve a good intercourse because of those secondary effects. The treatment with sildenafil was discontinued and the patient was given 6 mg yohimbine in combination with 30 mg clomipramine. He reported an improvement in IELT from 1 minute to 9 minutes, without headaches or apparition of low blood pressure, and was able to achieve the intercourse with a good erection without any difficulty.

In summary, it was thus observed that treatment with the combination of clomipramine and yohimbine led to a higher increase in IELT than treatment with only clomipramine. At the same time, fewer adverse side effects were reported with the combination of clomipramine with yohimbine than with either of the two single agents.

The invention claimed is:

1. A method for treating premature ejaculation in a subject in need thereof, the method comprising:
   administering to the subject an effective amount of a pharmaceutical composition comprising clomipramine (3-(3-chloro-10,11-dihydro-5H-dibenzo[b,f]azepin-5-yl)-N,N-dimethylpropan-1-amine) or a pharmaceutically acceptable salt form thereof and yohimbine (17α-hydroxy-yohimban-16α-carboxylic acid methyl ester) or a pharmaceutically acceptable salt form thereof wherein the composition comprises clomipramine in a range of from 5 to 150 mg, yohimbine in a range of from 5 to 150 mg, and clomipramine and yohimbine are present in a molar ratio in a range of from 0.2 to 5.

2. The method of claim 1, wherein the composition comprises the clomipramine in a range of from 10 to 50 mg.

3. The method of claim 1, wherein the composition comprises yohimbine in a range of from 10 to 50 mg.

4. The method of claim 1, wherein the composition is administered once per day, twice per day, or three times per day to the subject who is suffering from premature ejaculation.

5. The method of claim 1, wherein the composition is administered orally.

6. The method of claim 1, wherein the administering of the composition is performed by keeping a peak plasma level of clomipramine at 20 ng/ml or higher.

7. The method of claim 1, wherein the administering of the composition is performed by keeping a plasma level of yohimbine at 50 ng/ml or higher.

8. The method of claim 1, wherein the subject is suffering from primary or secondary premature ejaculation.

9. A method for treating premature ejaculation, the method comprising:
    administering an effective amount of clomipramine or a pharmaceutically acceptable salt form thereof and yohimbine or a pharmaceutically acceptable salt form thereof to a patient suffering from premature ejaculation wherein the amount of clomipramine is in a range of from 5 to 150 mg, yohimbine is in a range of from 5 to 150 mg, and clomipramine and yohimbine are administered in a molar ratio in a range of from 0.2 to 5.

10. The method of claim 1, wherein the composition comprises the clomipramine in a range of from 20 to 40 mg.

11. The method of claim 1, wherein the composition comprises yohimbine in a range of from 20 to 40 mg.

12. The method of claim 1, wherein the clomipramine and yohimbine are present in a molar ratio in a range of from 0.8 to 1.5.

13. The method of claim 1, wherein the administering clomipramine and yohimbine improves the efficacy of clomipramine by increasing intravaginal ejaculation latency time (IELT) compared to administering clomipramine without yohimbine.

14. The method of claim 1, wherein the administering clomipramine and yohimbine reduces side-effects associated with clomipramine compared to administering clomipramine without yohimbine.

* * * * *